(12) United States Patent
Ishimaru

(10) Patent No.: US 9,778,166 B2
(45) Date of Patent: Oct. 3, 2017

(54) MICROPARTICLE MEASUREMENT DEVICE

(71) Applicant: NATIONAL UNIVERSITY CORPORATION KAGAWA UNIVERSITY, Takamatsu-shi, Kagawa (JP)

(72) Inventor: Ichiro Ishimaru, Takamatsu (JP)

(73) Assignee: NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 0 days.

(21) Appl. No.: 15/117,536

(22) PCT Filed: Feb. 20, 2015

(86) PCT No.: PCT/JP2015/054786
§ 371 (c)(1),
(2) Date: Oct. 28, 2016

(87) PCT Pub. No.: WO2015/125918
PCT Pub. Date: Aug. 27, 2015

(65) Prior Publication Data
US 2017/0045437 A1 Feb. 16, 2017

(30) Foreign Application Priority Data
Feb. 24, 2014 (JP) ................. 2014-033242

(51) Int. Cl.
G01N 21/00 (2006.01)
G01N 15/14 (2006.01)
(Continued)

(52) U.S. Cl.
CPC .......... *G01N 15/1436* (2013.01); *B01L 3/502* (2013.01); *G01N 15/1434* (2013.01);
(Continued)

(58) Field of Classification Search
CPC .............. G01B 9/0209; G01B 9/02057; G01B 11/2441; G01B 2290/45; G01B 2290/70;
(Continued)

(56) References Cited

U.S. PATENT DOCUMENTS 5,208,651 A   5/1993   Buican
5,504,336 A   4/1996   Noguchi
(Continued)

FOREIGN PATENT DOCUMENTS

CA   2827726 A1   8/2012
CN   1350179 A    5/2002
(Continued)

OTHER PUBLICATIONS

May 19, 2015 International Search Report issued in International Patent Application No. PCT/JP20151054786.
(Continued)

*Primary Examiner* — Michael P Stafira
(74) *Attorney, Agent, or Firm* — Oliff PLC

(57) ABSTRACT

In a microparticle measurement device, a sample is passed through each channel in a multi-flow channel, and a predetermined linear area is illuminated with light. Measurement light originating from a microparticle in the sample, such as scattered or fluorescent light, is shaped into a parallel beam by an objective lens and passes through a first and second transmission portions. The beams transmitted through these two portions are converged as first and second measurement beams onto the same straight line by a cylindrical lens. The intensity of the interference light formed by these beams is detected with a detector. Meanwhile, the light emitted from the light source and passing through the multi-flow channel without hitting the microparticle falls through the objective lens onto a non-reflection portion and does not travel toward the cylindrical lens. Accordingly, only the interference light
(Continued)

formed by the measurement beams is allowed to fall onto the detector.

15 Claims, 9 Drawing Sheets

(51) Int. Cl.
| | | |
|---|---|---|
| *B01L 3/00* | (2006.01) | |
| *G01N 21/64* | (2006.01) | |
| *G01N 21/65* | (2006.01) | |
| *G01N 15/00* | (2006.01) | |
| *G01N 15/10* | (2006.01) | |
| *G01N 21/25* | (2006.01) | |

(52) U.S. Cl.
CPC ....... *G01N 15/1459* (2013.01); *G01N 21/645* (2013.01); *B01L 2200/0647* (2013.01); *B01L 2300/0609* (2013.01); *B01L 2300/0654* (2013.01); *B01L 2300/0861* (2013.01); *B01L 2300/168* (2013.01); *G01N 21/253* (2013.01); *G01N 21/65* (2013.01); *G01N 2015/0073* (2013.01); *G01N 2015/1006* (2013.01); *G01N 2021/6421* (2013.01); *G01N 2021/6463* (2013.01); *G01N 2201/06113* (2013.01)

(58) Field of Classification Search
CPC ............ G01B 9/02007; G01B 9/02027; G01B 9/0201; G01B 9/02039; G01B 9/02068; G01B 9/02077; G01B 11/0675; G01B 11/06; G01B 9/02
See application file for complete search history.

(56) References Cited

U.S. PATENT DOCUMENTS

| | | | | |
|---|---|---|---|---|
| 5,694,216 | A * | 12/1997 | Riza ................... | G01B 9/02004 356/485 |
| 8,830,451 | B1 | 9/2014 | Graves et al. | |
| 2002/0046949 | A1 | 4/2002 | Nakamura et al. | |
| 2005/0046865 | A1* | 3/2005 | Brock ................ | G01B 9/02057 356/495 |
| 2009/0101847 | A1 | 4/2009 | Furuki et al. | |
| 2009/0116005 | A1 | 5/2009 | Furuki et al. | |
| 2011/0122412 | A1 | 5/2011 | Joo et al. | |
| 2013/0050782 | A1 | 2/2013 | Heng et al. | |
| 2013/0214176 | A1 | 8/2013 | Graves et al. | |
| 2014/0336062 | A1 | 11/2014 | Graves et al. | |
| 2015/0276575 | A1* | 10/2015 | Takeuchi ........... | G01N 15/1434 356/338 |

FOREIGN PATENT DOCUMENTS

| | | |
|---|---|---|
| CN | 101413866 A | 4/2009 |
| CN | 101424612 A | 5/2009 |
| EP | 2051061 A2 | 4/2009 |
| EP | 2056090 A2 | 5/2009 |
| EP | 2504686 A1 | 10/2012 |
| EP | 2678660 A1 | 1/2014 |
| JP | H06-331441 A | 12/1994 |
| JP | 2002-195949 A | 7/2002 |
| JP | 2009-098049 A | 5/2009 |
| JP | 2009-115473 A | 5/2009 |
| JP | 2013-511714 A | 4/2013 |
| JP | 2014-507662 A | 3/2014 |
| KR | 20020032361 A | 5/2002 |
| KR | 20090039618 A | 4/2009 |
| KR | 20090045845 A | 5/2009 |
| WO | 2011/062555 A1 | 5/2011 |
| WO | 2012/115979 A1 | 8/2012 |
| WO | 2013/191772 A1 | 12/2013 |

OTHER PUBLICATIONS

Aug. 30, 2016 International Preliminary Report on Patentability issued in International Patent Application No. PCT/JP2015/054786.
"Cytometry", [online], Beckman Coulter, [accessed on Sep. 30, 2013], the Internet <URL: http://www.bc-cytometry.com/cytometry.html>.
Masaru Fujiwara et al. "Ultra Compact One-Shot Spectroscopic Tomography Imaging Device for the Daily-Life Environment (First Report)—Feasibility Study With the Transmission-Type Relative-Inclined Phase-Shifter". Dai 60 Kai JSAP Spring Meeting Koen Yokoshu, Mar. 11, 2013, p. 03-103.
Hiroaki Kobayashi et al. "Development of Compact Infrared Spectral Imager". Intelligent Mechatronics Workshop Koen Ronbunshu, Aug. 27, 2013, vol. 18, ROMBUNNO.M2-5.
Tomohiro Uraki et al. "Proposal of the One-Shot Real-Time Fourier Spectroscopic Imaging". Optics & Photonics Japan Koen Yokoshu, Nov. 8, 2010, vol. 2010.
Daisuke Kojima et al. "Imaging-Type One-Shot Fourier Spectroscopic Imaging for High Time-Resolution". 2011 Nendo The Japan Society For Precision Engineering Shunki Taikai Gakujutsu Koenkai Koen Ronbunshu, Mar. 1, 2011, pp. 1059-1060.

* cited by examiner

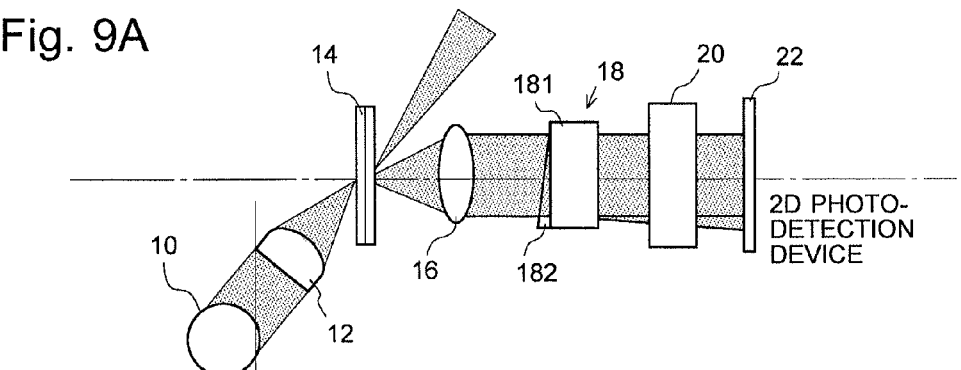
Fig. 9A
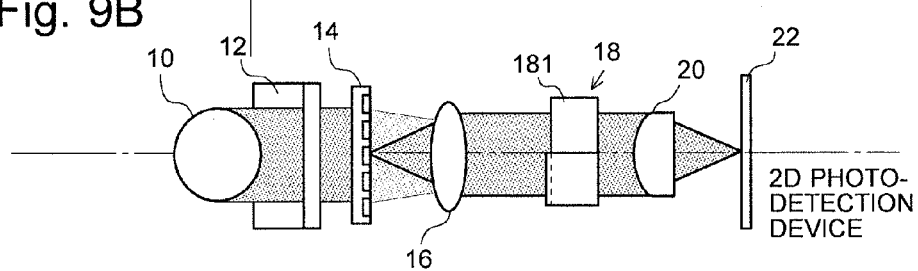
Fig. 9B
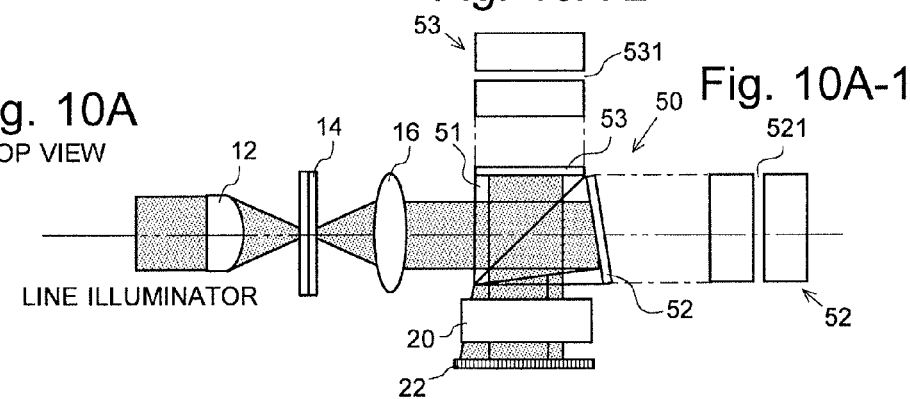
Fig. 10A TOP VIEW
Fig. 10A-2
Fig. 10A-1
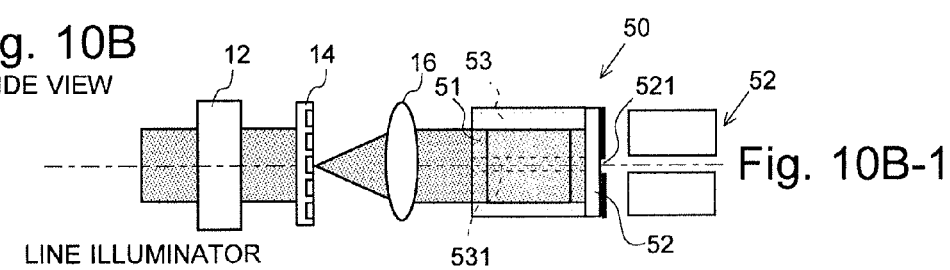
Fig. 10B SIDE VIEW
Fig. 10B-1

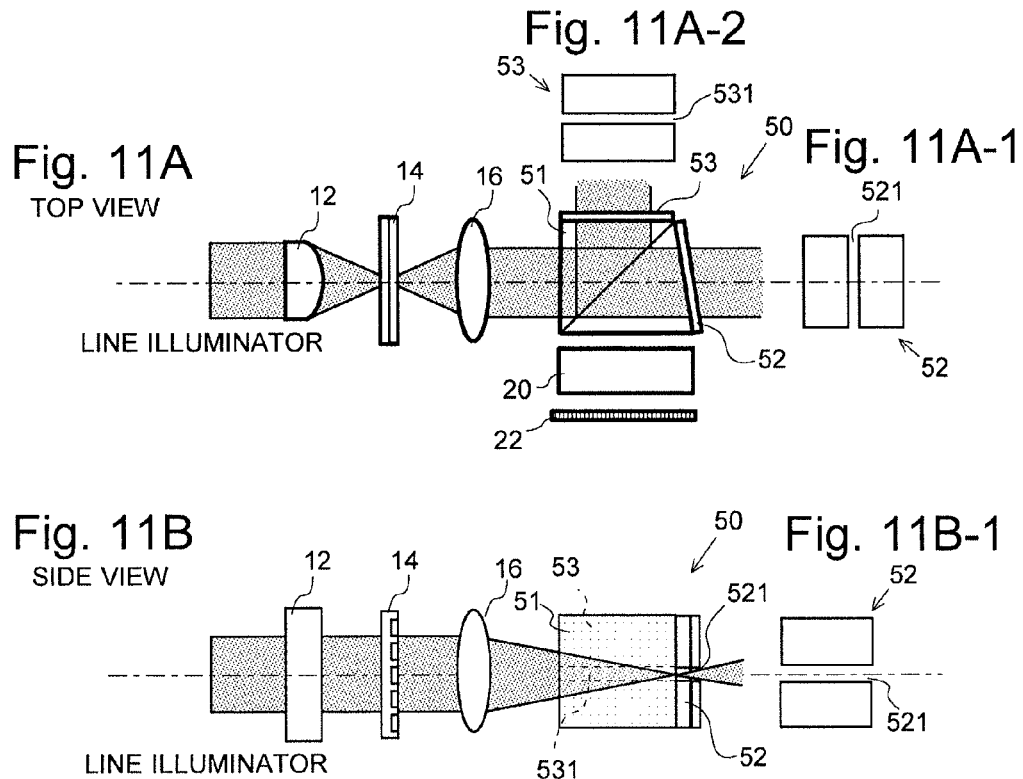
Fig. 11A TOP VIEW
Fig. 11A-1
Fig. 11A-2
Fig. 11B SIDE VIEW
Fig. 11B-1
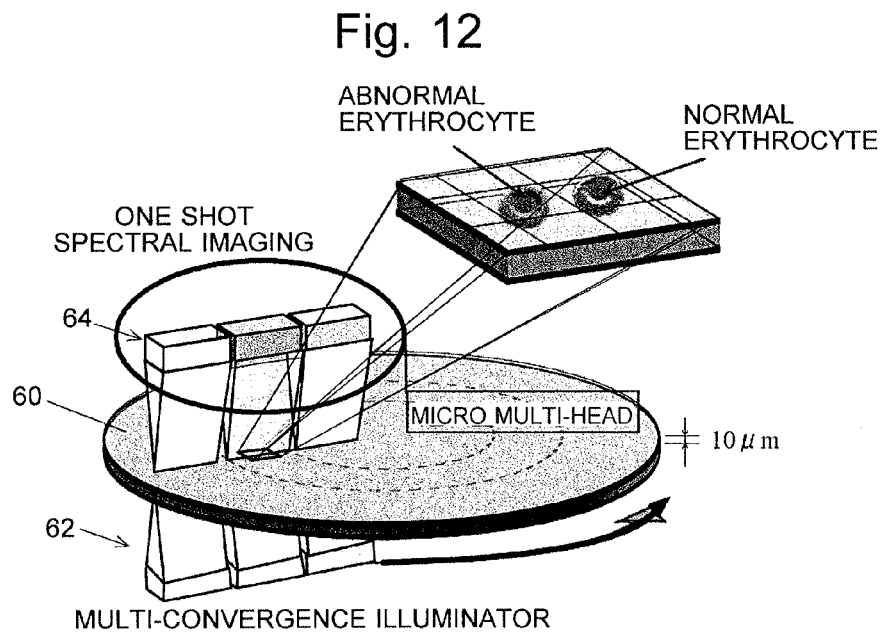
Fig. 12

Fig. 13A
NEAR-INFRARED IMAGE
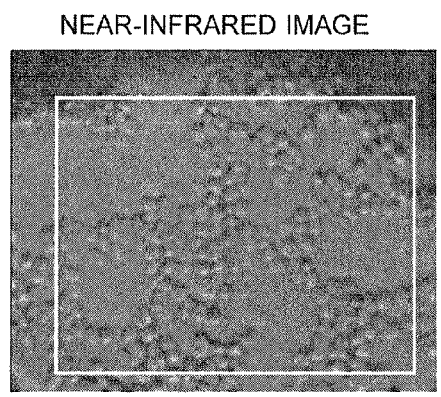
VISIBLE IMAGE
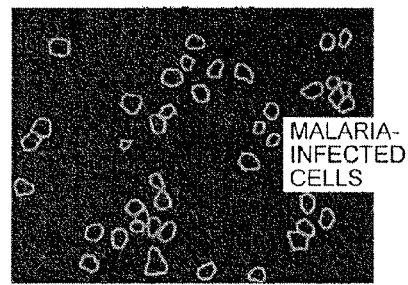
Fig. 13C
Fig. 13B
INTERFERENCE INTENSITY
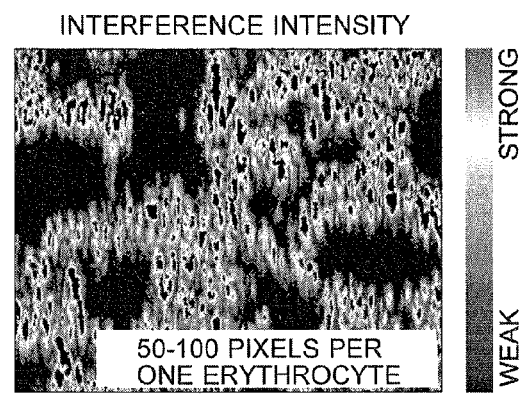
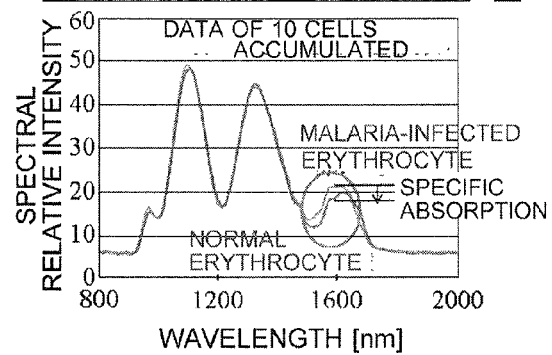
Fig. 13D

CONVERGING ILLUMINATION

CONVERGING ILLUMINATION

MICROPARTICLE MEASUREMENT DEVICE

TECHNICAL FIELD

The present invention relates to a microparticle measurement device used in flow cytometers, cell sorters or similar devices.

BACKGROUND ART

A flow cytometer is one type of device used for analyzing the kind, size, shape, structure and other characteristics of microparticles, such as cells, microorganisms or microbeads. In the flow cytometer, microparticles arranged in a row are passed through a flow channel. When passing through a specific section of the channel, the microparticles are irradiated with light. Then, the light that originates from those microparticles (e.g. scattered light or fluorescent light) is detected to determine a characteristic of each microparticle (see Non Patent Literature 1).

For example, in the case of detecting a fluorescence emitted from a cell, the cell labelled with a fluorescent dye is irradiated with excitation light (e.g. laser light), and the fluorescence emitted from the fluorescent dye due to the irradiation is detected through a wavelength-selecting device, such as a bandpass filter or dichroic mirror. In this method, a plurality of fluorescent emissions in different wavelength bands can be detected by using a plurality of wavelength-selecting devices with different wavelength selection bands and providing a separate photodetector for each wavelength-selecting device to detect the thereby selected light. Accordingly, if a fluorescent dye having a different fluorescence wavelength band is used for the labelling of each kind of cell, it is possible to determine optical characteristics of each kind of cell.

CITATION LIST

Non Patent Literature

Non Patent Literature 1: "Cytometry", [online], Beckman Coulter, [accessed on Sep. 30, 2013], the Internet

SUMMARY OF INVENTION

Technical Problem

The previously described conventional method requires the same number of wavelength-selecting devices and photodetectors as the fluorescent wavelength bands to be measured. Accordingly, increasing the number of fluorescent wavelength bands leads to a corresponding increase in the number of wavelength-selecting devices and photodetectors, which in turn requires the entire device to be larger in order to secure optical paths from the wavelength-selecting devices to the photodetectors.

Additionally, since the combination of the wavelength band of the excitation light and that of the fluorescence is fixed for each kind of fluorescent dye, the fluorescent dyes are normally selected in such a manner that the wavelength of the excitation light for one fluorescent dye does not overlap the fluorescent wavelength band of any other fluorescent dye so that the fluorescence emitted from each fluorescent dye will be separated from not only the excitation light for the dye concerned but also those used for the other fluorescent dyes. However, if there are many fluorescent dyes as the measurement target, the fluorescent wavelength band of one fluorescent dye may possibly overlap the excitation wavelength band for another fluorescent dye, making it difficult to isolate and detect only the fluorescence intensity.

Furthermore, the conventional flow cytometer has a low level of processing capability since microparticles are arranged in a row and passed through a single channel, with each individual microparticle irradiated with light when passing through a specific detection area. Although it may be possible to increase the flow velocity of the microparticles in the channel to improve the processing capability, there is an upper limit of the flow velocity, since increasing the flow velocity causes microparticles to undergo damage or breakage.

The problem to be solved by the present invention is to provide a microparticle measurement device capable of simultaneously measuring an optical characteristic of a plurality of microparticles at high speeds.

Solution to Problem The microparticle measurement device according to the present invention developed for solving the previously described problem includes:

a) a transparent sample container for holding a sample containing microparticles;

b) a light-casting device for casting a light onto a linear area of the sample held in the sample container;

c) a splitting optical system for splitting measurement light originating from a microparticle in the linear area into a first measurement beam and a second measurement beam;

d) an optical path difference creator for creating an optical path difference between the first measurement beam and the second measurement beam;

e) a cylindrical lens for converging the first measurement beam and the second measurement beam onto the same straight line to make the two beams interfere with each other;

f) a detector for detecting the intensity distribution of the interference light formed by the first measurement beam and the second measurement beam along a longitudinal direction of the same straight line; and g) a processor for producing an interferogram of the light originating from the microparticle based on the intensity distribution of the interference light detected by the detector, and for obtaining a spectrum by Fourier-transforming the interferogram, and the microparticle measurement device further including, a split prevention device for preventing light which is emitted from the light-casting device and passing through the sample container from being split by the splitting optical system.

In a microparticle measurement device according to the first mode of the present invention, the splitting optical system includes: an optical member having a first transmission portion with an entrance surface and an exit surface parallel to each other, a second transmission portion, located next to the first transmission portion, having an entrance surface and an exit surface forming a wedge-like shape with one of the two surfaces inclined to the other, as well as a non-transmission portion which does not allow the passage of light; and an optical element for shaping the measurement light originating from the microparticle irradiated with the light from the light-casting device into a parallel beam falling onto both the entrance surface of the first transmission portion and the entrance surface of the second transmission portion, and for making the light which is emitted from the light-casting device and passing through the sample container fall onto the non-transmission portion. In this case, the non-transmission portion constitutes the split prevention device, while the first transmission portion and the second transmission portion constitute the optical path difference creator.

In the present configuration, the measurement light passing through the first transmission portion becomes the first measurement beam, and the measurement light passing through the second transmission portion becomes the second measurement beam.

In a microparticle measurement device according to the second mode of the present invention, the splitting optical system includes: an optical member having a first transmission portion with an entrance surface and an exit surface parallel to each other, as well as a second transmission portion, located next to the first transmission portion, having an entrance surface and an exit surface forming a wedge-like shape with one of the two surfaces inclined to the other; and an optical element for shaping the measurement light originating from the microparticle irradiated with the light from the light-casting device into a parallel beam falling onto both the entrance surface of the first transmission portion and the entrance surface of the second transmission portion, and the split prevention device includes a filter, located between the optical element and the entrance surfaces of the first and second transmission portions, for blocking the light from the light-casting device. In this case, the first transmission portion and the second transmission portion constitute the optical path difference creator.

In the present configuration, both the light which passes through the sample container without hitting the microparticle among the light (excitation light) cast from the light-casting device into the sample held in the sample container, and the light which has the same wavelength as that of the excitation light among the light resulting from an interaction between the microparticle and the excitation light are blocked by the filter, while any ray of light having a different wavelength from the excitation light, such as Raman scattered light or fluorescent light, is allowed to pass through the filter and enter the first and second transmission portions. Accordingly, in the present configuration, the light passing through the first transmission portion among the light originating from the microparticle becomes the first measurement beam, while the light passing through the second transmission portion becomes the second measurement beam.

As the aforementioned filter, any one of the following filters, or a combination of two or more of them can be used: an edge filter (short-pass filter or long-pass filer) for blocking light at wavelengths longer or shorter than a specific wavelength, a notch filter for blocking light within a specific wavelength range, and a bandpass filter for allowing the passage of light within a specific wavelength range. In a microparticle measurement device according to the third mode of the present invention, the splitting optical system includes: a reflection optical member having a first reflection plane with a first non-reflection area and a second reflection plane with a second non-reflection area; and an optical element for shaping the measurement light originating from the microparticle irradiated with the light from the light-casting device into a parallel beam, for splitting the parallel beam into two beams respectively falling onto the first reflection plane and the second reflection plane, and for making the light which is emitted from the light-casting device and passing through the sample container fall onto the first non-reflection area and the second non-reflection area. In this case, the first non-reflection area and the second non-reflection area constitute the split prevention device.

The optical path difference creator may include a driving device for moving the first reflection plane and the second reflection plane relative to each other. It may also be realized by making one of the first and second reflection planes inclined from a plane perpendicular to the optical axis of the measurement beams.

In the present case, the measurement light reflected by the first reflection plane becomes the first measurement beam, and the measurement light reflected by the second reflection plane becomes the second measurement beam.

The light cast from the light-casting device into the sample should preferably be a beam of light having a width approximately equal to the size of the microparticle.

The sample container may be provided with a measurement channel with a plurality of flow channels arranged parallel to each other, with the size of the flow channels determined so as to allow the microparticles to flow in parallel, with one microparticle in each channel. In this case, the light-casting device should preferably cast the linear beam of light onto a linear area encompassing the plurality of flow channels.

The sample container may be a holder plate in the form of a disc having a top surface to which a sample containing microparticles is to be applied, along with a rotating device for rotating the holder plate about the center of the disc. In this case, the light-casting device should preferably cast light which illuminates a linear area extending radially from the rotation center toward the circumferential edge of the holder plate. By this configuration, the sample applied to the top surface of the holder plate can be entirely irradiated with the light by having the holder plate rotated one time by the rotating device.

Advantageous Effects of the Invention

In the microparticle measurement device according to the present invention, a linear beam of light is cast into a sample held in the sample container. Accordingly, a plurality of microparticles existing within the illumination area are collectively irradiated with the light. Since the light which is emitted from the light-casting device and passing through the sample container is prevented from being split by the splitting optical system, only the measurement light originating from each of the microparticles is split into the first measurement beam and the second measurement beam, and the intensity distribution of the interference light formed by the first and second measurement beams is detected. Based on the detected intensity distribution of the interference light formed by the first and second measurement beams, an interferogram is produced, and this interferogram is Fourier-transformed to obtain a spectrum. In this manner, according to the present invention, it is possible to simultaneously measure an optical characteristic of a plurality of microparticles at high speeds.

In the microparticle measurement device according to the first mode of the present invention, the light originating from a microparticle, such as the scattered light or fluorescent light, is shaped into a parallel beam by the optical element and passed through both the first and second transmission portions, whereby two beams with a continuous optical path difference are produced. These beams are converged onto the same straight line by the cylindrical lens, and the intensity distribution of the interference light along the longitudinal direction is detected by the detector. Accordingly, the spectrum of the light originating from the microparticle can be obtained by producing an interferogram from the intensity distribution and Fourier-transforming the interferogram. Among the light emitted from the light-casting device, the light which passes through the sample container falls onto the non-transmission portion, and therefore, is prevented from passing through the first and second transmission portions. Accordingly, the light which is emitted from the light-casting device and directly passing through the sample container without hitting the microparticle will not be detected by the detector, and the pure spectrum of the light originating from the microparticle can be obtained. Since a pure spectrum of the light originating from the microparticle can be obtained in this manner, the first mode of the present invention requires neither a means for dividing the light originating from the microparticle into component wavelengths, nor a means for separating fluorescence from the excitation light. Therefore, the entire device will not be significantly large.

In the microparticle measurement device according to the second mode of the present invention, both the light passing through the sample container among the light emitted from the light-casting device, and the light having the same wavelength as the light emitted from the light-casting device among the light originating from the microparticles in the sample are removed by the filter. Therefore, Raman scattered light, fluorescent light or other kinds of light having a different wavelength from the light cast from the light-casting device can be detected with a high level of sensitivity among the light originating from the microparticles.

In the microparticle measurement device according to the third mode of the present invention, the light originating from a microparticle, such as the scattered light or fluorescent light, is shaped into a parallel beam by the optical element. This beam is subsequently reflected by the first and second reflection planes, and the two resulting beams are given a continuous optical path difference by the optical path difference creator. These beams are converged onto the same straight line by the cylindrical lens, and the intensity distribution of the interference light is detected. Accordingly, the spectrum of the light originating from the microparticle can be obtained by producing an interferogram from the intensity distribution and Fourier-transforming the interferogram. Among the light emitted from the light-casting device, the light which passes through the sample container falls onto the first and second non-reflection areas, and therefore, will not be reflected by the first and second reflection planes. Accordingly, the light which is emitted from the light-casting device and directly passing through the sample container without hitting the microparticle will not be detected by the detector, and the pure spectrum of the light originating from the microparticle can be obtained. Since a pure spectrum of the light originating from the microparticle can be obtained in this manner, the third mode of the present invention requires neither a means for dividing the light originating from the microparticle into component wavelengths, nor a means for separating fluorescence from the excitation light. Therefore, the entire device will not be significantly large.

BRIEF DESCRIPTION OF DRAWINGS

FIG. 1A is a top view and FIG. 1B is a side view.

FIG. 3A is a top view, FIG. 3B is a perspective view, and FIG. 3C is a side view.

FIG. 4A is a top view, FIG. 4B is a perspective view, and FIG. 4C is a side view.

FIG. 5A is a top view and FIG. 5B is a side view.

FIG. 6A is a top view and FIG. 6B is a side view.

FIGS. 9A and 9B are model diagrams showing a microparticle measurement device according to the second embodiment of the present invention, where FIG. 9A is a top view and FIG. 9B is a side view.

FIGS. 10A, 10A-1, 10A-2, 10B and 10B-1 are model diagrams showing a microparticle measurement device according to the third embodiment of the present invention, where FIG. 10A is a top view, FIG. 10A-1 is a front view of the first reflection plane, FIG. 10A-2 is a front view of the second reflection plane, FIG. 10B is a side view with the cylindrical lens 20 and the two-dimensional array device 22 omitted, and FIG. 10B-1 is a front view of the first reflection plane.

FIGS. 11A, 11A-1, 11A-2, 11B and 11B-1 illustrate an optical path of the excitation light, where FIG. 11A is a top view, FIG. 11A-1 is a front view of the first reflection plane, FIG. 11A-2 is a front view of the second reflection plane, FIG. 11B is a side view with the cylindrical lens 20 and the two-dimensional array device 22 omitted, and FIG. 11B-1 is a front view of the first reflection plane.

FIG. 12 is a perspective view of a microparticle measurement device according to the fourth embodiment of the present invention.

FIGS. 13A-13D show measurement results, where FIG. 13A is a near-infrared image, FIG. 13B is an interference intensity image, FIG. 13C is a visible image, and FIG. 13D is a spectrum of the scattered light.

FIG. 14A is a top view and FIG. 14B is a side view.

DESCRIPTION OF EMBODIMENTS

Specific embodiments of the present invention are hereinafter described with reference to the drawings.

First Embodiment

Figure 1A:
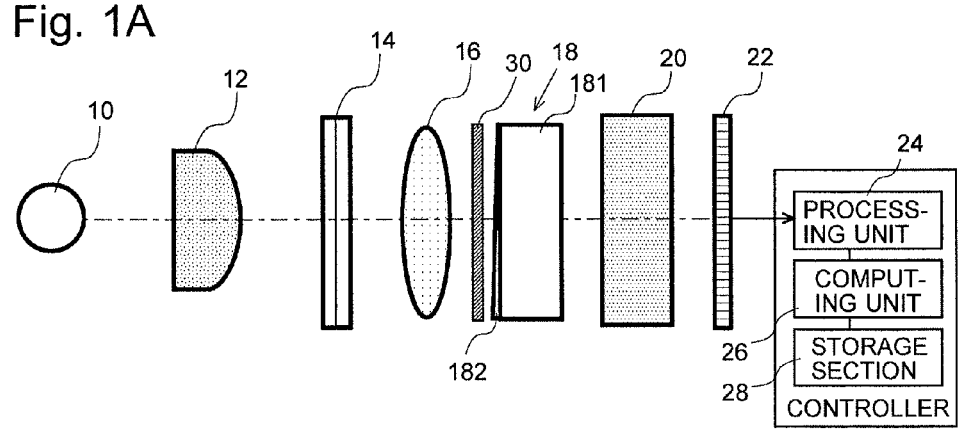
FIGS. 1A and 1B are model diagrams showing a microparticle measurement device according to the first embodiment of the present invention, where
Figure 1B:
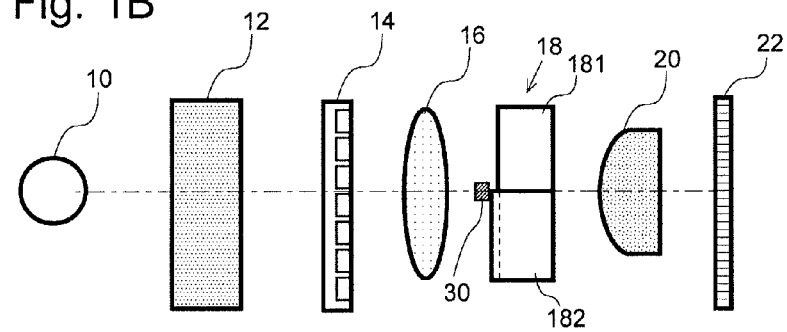

FIGS. 1A and 1B show schematic configuration diagrams of a microparticle measurement device according to the first embodiment of the present invention. FIG. 1A is a top view, and FIG. 1B is a side view. This optical characteristic measurement device includes a light source 10, a cylindrical lens 12, a multi-flow channel 14, an objective lens 16, a transmission phase shifter 18, a cylindrical lens 20 serving as an imaging lens, and a two-dimensional array device 22 (which corresponds to the detector in the present invention), such as a two-dimensional CCD camera.

Figure 2:
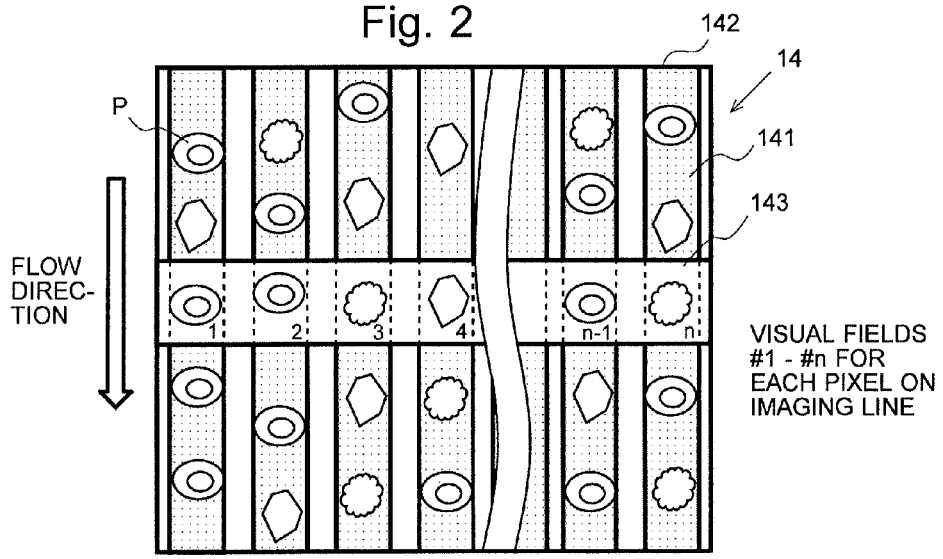
FIG. 2 is an overall configuration diagram of a multi-flow channel.
Figure 3A:
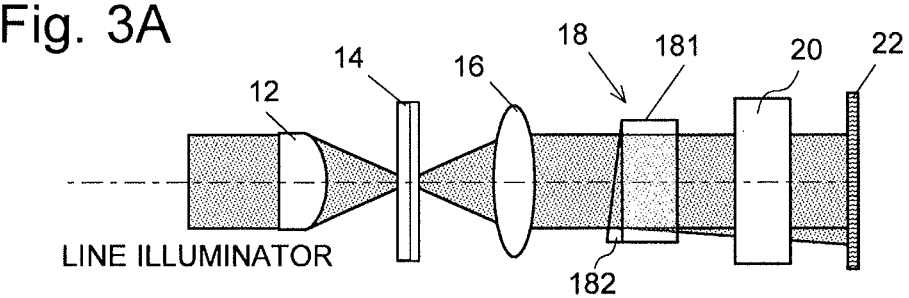
FIGS. 3A-3C illustrate an optical path of the excitation light, where
Figure 3B:
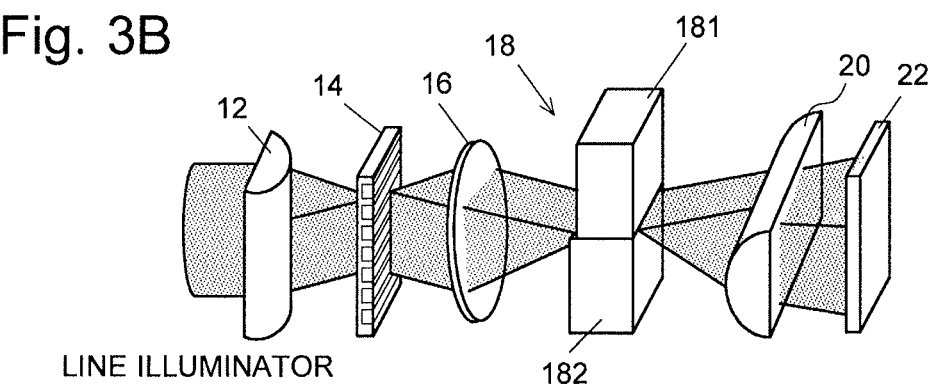
Figure 3C:
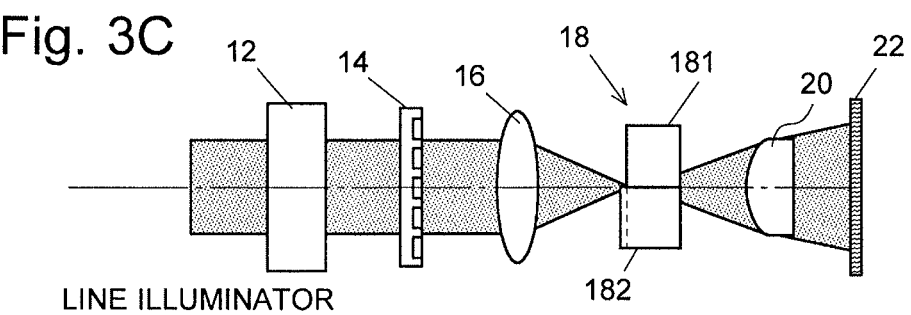

The multi-flow channel 14 corresponds to the sample container in the present invention. As shown in FIG. 2, it consists of a rectangular plate 142 with a plurality of flow channels 141 having an extremely small width. The width of each channel 141 is appropriately set according to the size of the microparticles of interest. The channels 141 are parallel to each other, with one detection window 143 formed in each channel 141. The detection window 143 is made of a transparent material, such as a glass or plastic material. The detection windows 143 in the plurality of channels 141 lie on the same straight line. The arrangement of the cylindrical lens 12 and the multi-flow channel 14 is determined so that the light from the light source 10 is converged onto the detection windows 143 by the cylindrical lens 12. In this manner, in the present embodiment, a linear beam of light is cast onto the multi-flow channel 14. The light source 10 and the cylindrical lens 12 constitute the light-casting device.

On the upstream side of the multi-flow channel 14, a sample supplier (not shown) for supplying a liquid sample containing microparticles into the channels 141 is provided. The sample supplier also introduces a sheath liquid into each channel 141 of the multi-flow channel 14 along with the microparticle-containing sample in such a manner that a laminar flow maintained at a specific flow velocity is formed within the channel.

For example, the two-dimensional array device 22 is a two-dimensional CCD camera. The light-receiving surface of the two-dimensional array device 22 is located at the focal plane of the cylindrical lens 20. The detection signals of the two-dimensional array device 22 are fed to a processing unit 24. The processing unit 24 produces an interferogram from the detection signals fed from the two-dimensional array device 22. The interferogram is Fourier-transformed mathematically by a computing unit 26. As a result, a spectral characteristic (spectrum) which is the relative intensity of the measurement light at each wavelength is obtained.

The transmission phase shifter 18 is a plate-like optical member having a roughly rectangular overall shape with a first transmission portion 181 and a second transmission portion 182, both of which are transmission optical members. The first transmission portion 181 is an optical member having a uniform thickness with its entrance surface and exit surface parallel to each other. On the other hand, the second transmission portion 182 is a wedge-shaped optical member with its entrance surface inclined to that of the first transmission portion 181 and its exit surface lying on the same plane as the exit surface of the first transmission portion 181. In the present embodiment, the entrance surface of the second transmission portion 182 is inclined in such a manner that the thickness of the second transmission portion 182 at the boundary surface between the first transmission portion 181 and the second transmission portion 182 gradually decreases from one side to the other.

The inclination angle of the entrance surface of the second transmission portion 182 is determined by the amount of phase shift (which depends on the wavenumber resolution) and the sampling interval at each pixel of the two-dimensional array device 22, although a slight deviation is permissible.

Each of the first and second transmission portions 181 and 182 may be created as a separate optical member. Alternatively, the lower half area of a plate-shaped optical member may be machined to form the second transmission portion 182 with the inclined entrance surface.

A shielding plate 30 is placed on the entrance side of the transmission phase shifter 18 near the boundary between the first and second transmission portions 181 and 182. The shielding plate 30 has an extremely small width of a few millimeters to tens of micrometers covering an area near the boundary between the first and second transmission portions 181 and 182, and consists of a member that does not allow the transmission of the light from the light source 10. The shielding plate 30 corresponds to the split prevention means (non-transmission portion) in the present invention.

The optical operation of the present measurement device is hereinafter described with reference to FIGS. 3A-6B.

Initially, an optical path of the light emitted from the light source to the cylindrical lens 12 (excitation light) is described with reference to FIGS. 3A-4C, each of which shows the measurement device with the shielding plate 30 removed. The light radiated from the light source 10 and incident on the cylindrical lens 12 is converged onto the detection windows 143 of the multi-flow channel 14. As a result, a flux of measurement light (e.g. fluorescent or scattered light) originates from the microparticles P passing by the detection windows 143 (see FIG. 2). The flux of measurement light falls onto the objective lens 16 and is shaped into a parallel beam, which falls onto the first and second transmission portions 181 and 182 of the transmission phase shifter 18. Meanwhile, a portion of the light incident on the detection windows 143 directly passes through the channels 141 without hitting the microparticles, and falls onto the objective lens 16. This portion of the light incident on the objective lens 16 is converged by the same lens 16 on an area near the boundary between the first and second transmission portions 181 and 182. After passing through the first and second transmission portions 181 and 182, the light becomes diffuse light and falls onto the cylindrical lens 20. Consequently, the light falls onto the light-receiving surface in the form of diffuse light with a certain breadth, without being converged by the cylindrical lens 20 (see FIGS. 3A-3C). Accordingly, the objective lens 16 corresponds to the optical element in the present invention.

By comparison, the flux of measurement light which has passed through the first and second transmission portions 181 and 182 are separated into first and second measurement beams, which fall onto the cylindrical lens 20. Since the entrance and exit surfaces of the first transmission portion 181 are parallel to each other, the first measurement beam incident on the cylindrical lens 20 is in phase when it is converged on a single straight line on the light-receiving surface of the two-dimensional array device 22. On the other hand, since the second transmission portion 182 has its entrance surface inclined to its exit surface, the second measurement beam falls onto the cylindrical lens 20 with its wave front inclined along the entrance surface. This beam still has its wave front similarly inclined when it is eventually converged on the aforementioned straight line on the light-receiving surface of the two-dimensional array device 22 (see FIGS. 4A-4C).

Figure 4A:
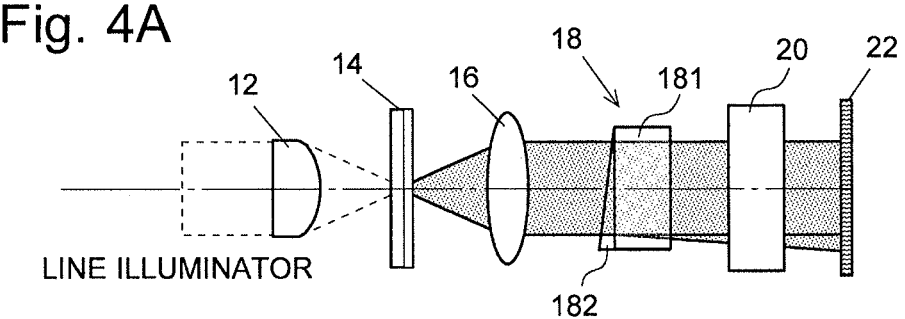
FIGS. 4A-4C illustrate an optical path of the light originating from a microparticle (measurement light), where
Figure 4B:
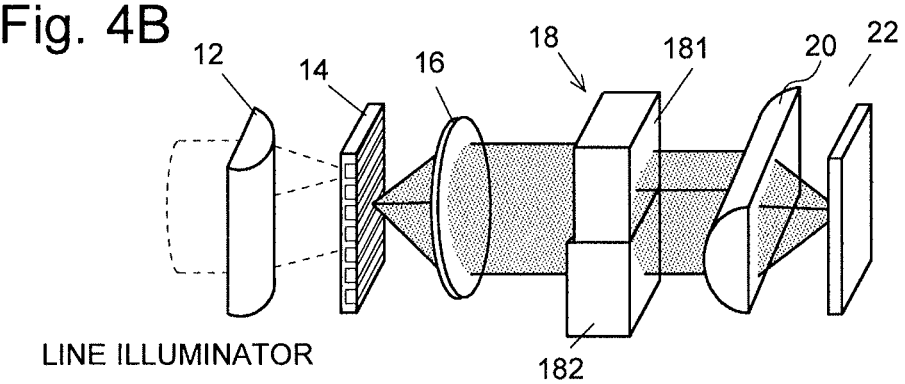
Figure 4C:
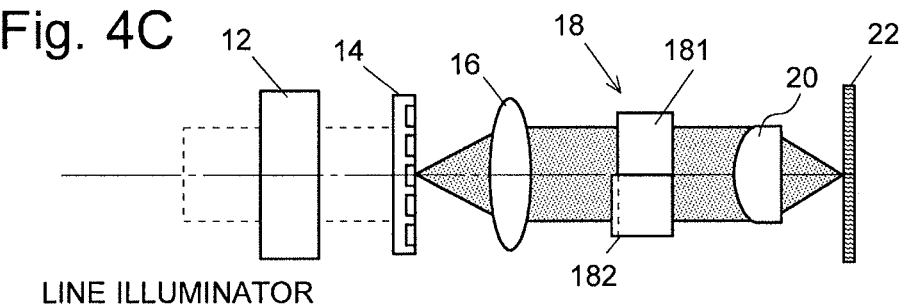

For ease of explanation, FIGS. 4A-4C only show the optical path of the measurement light originating from a microparticle passing by a single detection window 143. In the case where there are a plurality of microparticles simultaneously passing by two or more detection windows 143, the measurement light originating from the microparticle passing by any of those detection windows 143 follows a similar optical path to the previously described measurement light.

In this manner, both the measurement light originating from the microparticles and the other components of light fall onto the light-receiving surface of the two-dimensional array device 22 without being separated from each other.

Figure 5A:
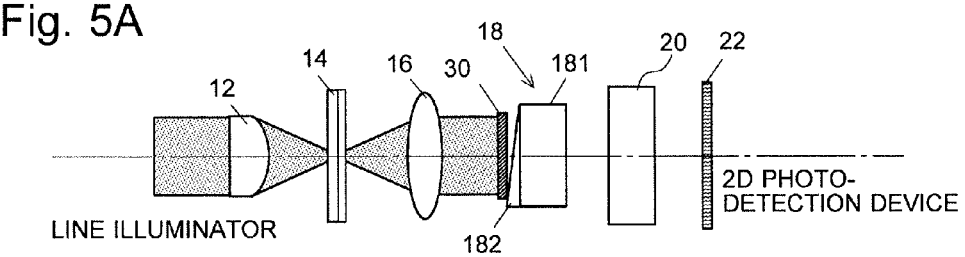
FIGS. 5A and 5B illustrate an optical path of the excitation light in the case where the excitation light is blocked halfway, where
Figure 5B:
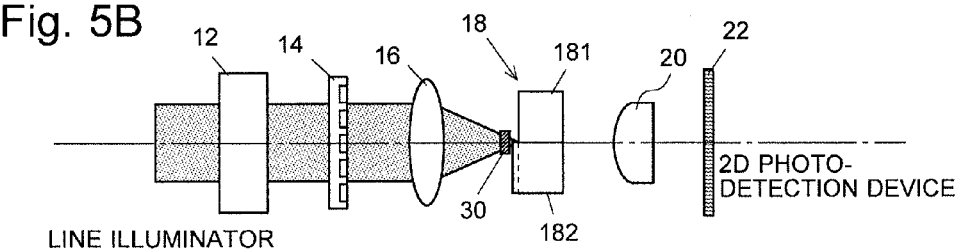
Figure 6A:
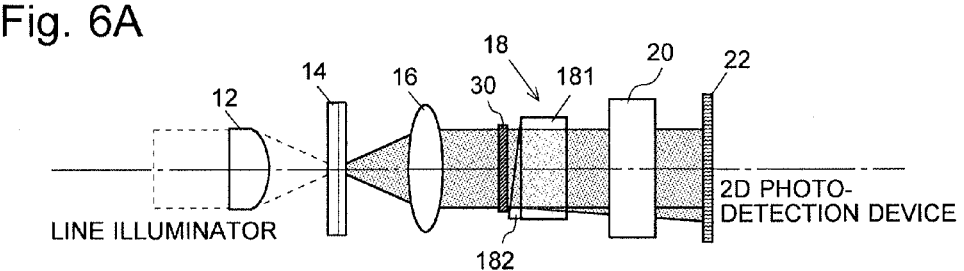
FIGS. 6A and 6B illustrate an optical path of the measurement light in the case where the excitation light is blocked halfway, where
Figure 6B:
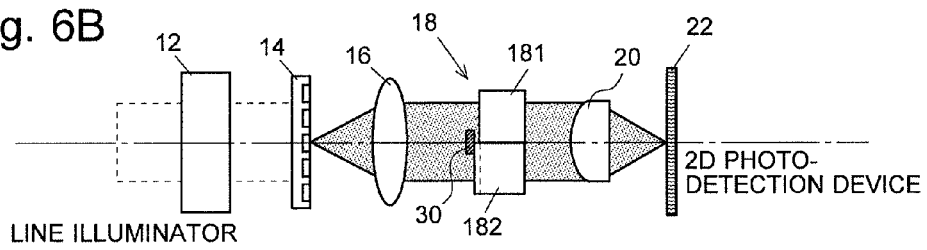

By comparison, as shown in FIGS. 5A and 5B, when the shielding plate 30 is placed near the boundary between the first and second transmission portions 181 and 182, the excitation light which has passed through the objective lens 16 is prevented from further travel by the shielding plate 30 and cannot enter the first and second transmission portions 181 and 182. On the other hand, the measurement light is only partially prevented from further travel by the shielding plate 30; a high proportion of the measurement light enters the first and second transmission portions 181 and 182, as shown in FIGS. 6A and 6B. Thus, only the first and second measurement beams fall onto the light-receiving surface of the two-dimensional photo-detection device 22 in a similar manner to the previously described case where no shielding plate 30 is provided. Upon receiving the first and second measurement beams on its light-receiving surface, the two-dimensional photo-detection device 22 sends the processing unit 24 electric signals corresponding to the intensity of the interference light formed by the two measurement beams. From those signals, an interferogram is produced by the processing unit 24. This interferogram is Fourier-transformed mathematically by the computing unit 26, and a spectral characteristic which is the relative intensity of the measurement light at each wavelength (spectral relative intensity) is obtained.

Figure 7:
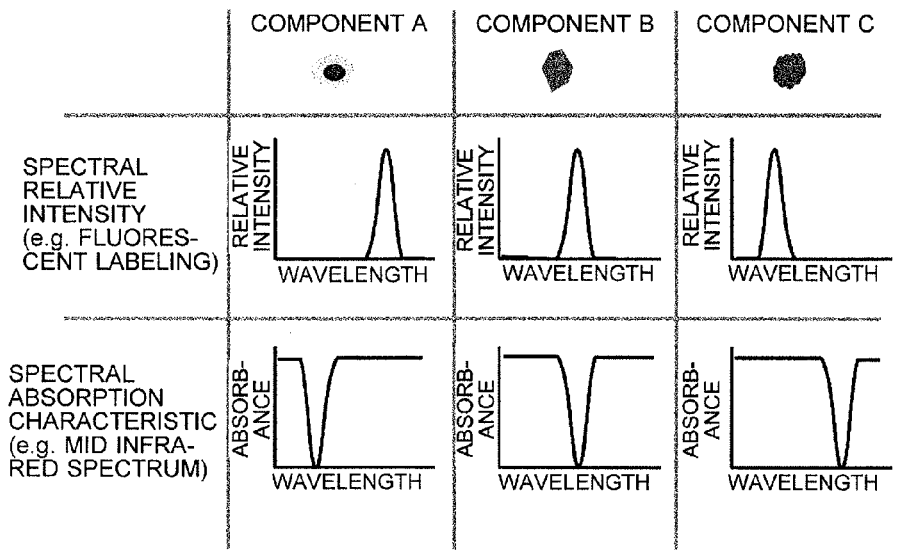
FIG. 7 is an image diagram showing the result of a measurement of the spectral relative intensity (fluorescence intensity) and the spectral absorption characteristic of microparticles obtained by the microparticle measurement device of the present embodiment.

FIG. 7 shows the spectral relative intensity and spectral absorption characteristic of microparticles (components A, B and C) measured with the previously described measurement device. Although only the spectral relative intensity was mentioned in the previous description, the spectral absorption characteristic can also be similarly determined.

Figure 8:
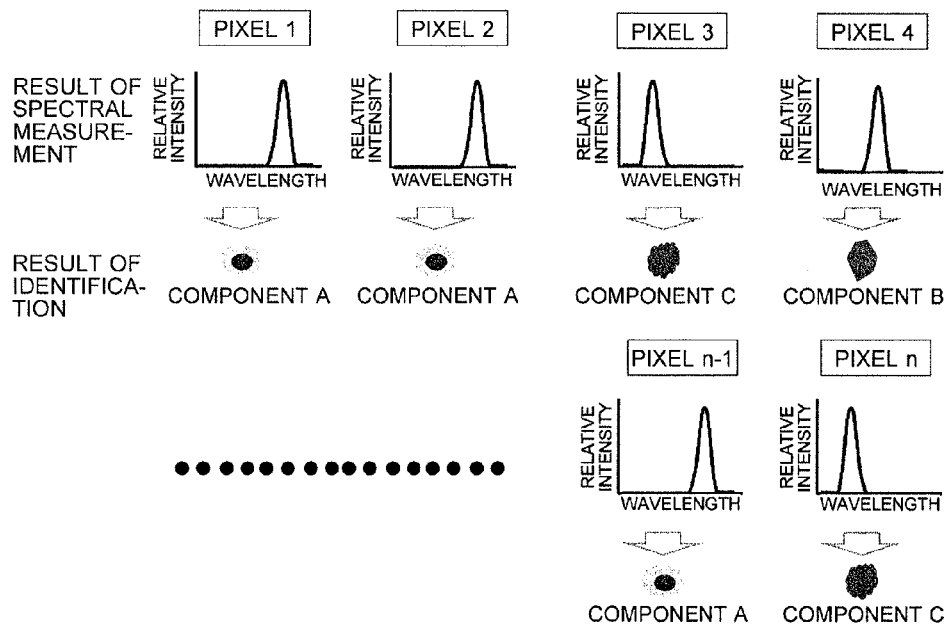
FIG. 8 is an image diagram showing a measurement result for each pixel.

FIG. 8 shows an example of the result of the spectral measurement obtained from pixels 1 through n of the two-dimensional array device which respectively correspond to the detection windows (1 through n) of the multi-flow channel.

In the present embodiment, the spectral relative intensity or/and the spectral absorption characteristic of each component is previously stored for each kind of component in a storage section 28. By comparing the spectral measurement result obtained at each pixel of the two-dimensional photo-detection device 22 with the spectral relative intensity stored in the storage section 28, the component which has passed by each detection window 143 is identified.

Second Embodiment

FIGS. 9A and 9B are schematic configuration diagrams of a microparticle measurement device according to the second embodiment of the present invention. The second embodiment differs from the first embodiment in the arrangement of the light source 10 and the cylindrical lens 12 in relation to the multi-flow channel 14. Specifically, the light source 10 and the cylindrical lens 12 in the second embodiment are arranged so that the optical path extending from the multi-flow channel 14 through the objective lens 16 to the transmission phase shifter 18 intersects with the optical path extending from the light source 10 through the cylindrical lens 12 to the multi-flow channel 14. In this arrangement, the portion of light which travels from the light source 10 through the cylindrical lens 12 into the multi-flow channel 14 and directly passes through the multi-flow channel 14 without hitting microparticles will not fall onto the objective lens 16. Accordingly, any ray of light other than the measurement light originating from the microparticles is prevented from falling onto the transmission phase shifter 18.

Third Embodiment

FIGS. 10A-11B show a microparticle measurement device according to the third embodiment of the present invention. This embodiment differs from the first embodiment in that a reflection phase shifter 50 is used in place of the transmission phase shifter. The reflection phase shifter 50, which is placed behind the objective lens 16, has a beam splitter 51, a first reflection plane 52 and a second reflection plane 53.

The side surface which is opposite from the entrance surface of the beam splitter 51 is slightly inclined to the entrance surface. The first reflection plane 52 is provided on this inclined side surface. The second reflection plane 53 is provided on one side surface located between the entrance surface of the beam splitter 51 and the first reflection plane 52. For example, the first and second reflection planes 52 and 53 are formed by depositing a metallic film (or similar layer) on the side surfaces of the beam splitter 51.

As shown in FIG. 10A-1, the first reflection plane 52 is divided into upper and lower areas, with a first non-reflection area 521 formed between the upper and lower reflection areas. The second reflection plane 53 is also similarly divided into upper and lower areas, as shown in FIG. 10A-2, with a second non-reflection area 531 formed between the upper and lower reflection areas. In the present embodiment, the non-reflection areas 521 and 531 are formed on the side surfaces of the beam splitter 51 by preventing the deposition of the metallic film (or similar layer) on these areas. Optical beams incident on the non-reflection areas 521 and 531 are allowed to pass through these areas.

In the present measurement device, the light radiated from the light source (not shown) and incident onto the cylindrical lens 12 is converged on the detection windows 143 of the multi-flow channel 14. The converged light linearly illuminates the sample liquid passing by the plurality of detection windows 143. As a result, measurement light, such as fluorescent or scattered light, originates from each microparticle P (see FIG. 2). The measurement light falls onto the objective lens 16 and is shaped into a parallel beam, which enters the beam splitter 51 of the reflection phase shifter 50. A portion of the measurement light which has entered the beam splitter 51 (first measurement beam) is transmitted through the joint surface of the beam splitter 51 toward the first reflection plane 52, while the remaining portion (second measurement beam) is reflected by the joint surface toward the second reflection plane 53. The first measurement beam directed toward the first reflection plane 52 is initially reflected by the first reflection plane 52 and subsequently reflected once more by the joint surface of the beam splitter 51, to be incident on the cylindrical lens 20. Similarly, the second measurement beam directed toward the second reflection plane 53 is initially reflected by the second reflection plane 53 and subsequently transmitted through the joint surface of the beam splitter 51, to be incident on the cylindrical lens 20. Since the first reflection plane 52 is inclined, the first measurement beam incident on the cylindrical lens 20 has an inclined wave front when it is converged on a single straight line on the light-receiving surface of the two-dimensional array device 22. On the other hand, since the second reflection plane 53 is not inclined, the second measurement beam incident on the cylindrical lens 20 is in phase when it is converged on the same straight line as the first measurement beam on the light-receiving surface of the two-dimensional array device 22.

On the other hand, as shown in FIGS. 11A and 11B, a portion of the light incident on the detection windows 143 directly passes through the channels 141, without hitting the microparticles, and falls through the objective lens 16 onto the beam splitter 15. The position of the joint surface in the beam splitter 51 of the reflection phase shifter 50 is set so that the light which travels from the light source through the detection windows 143 and the objective lens 16 will be converged on the first non-reflection area 521 of the first reflection plane 52 and the second non-reflection area 531 of the second reflection plane 53.

Accordingly, a portion of the light emitted from the light source and falling onto the objective lens 16 after directly passing through the detection windows 143 is transmitted through the joint surface of the beam splitter 51 and forwarded through the first non-reflection area 521 to the area behind the first reflection plane 52. Similarly, another portion of the light emitted from the light source and falling onto the objective lens 16 after directly passing through the detection windows 143 is reflected by the joint surface of the beam splitter 51 and forwarded through the second non-reflection area 531 to the area behind the second reflection plane 53. In this manner, only the measurement light originating from the microparticles is directed toward the cylindrical lens 20 and detected by the two-dimensional photodetection device 22 in a similar manner to the first embodiment.

Fourth Embodiment

FIG. 12 shows the overall configuration of a microparticle measurement device according to the fourth embodiment of the present invention. The present embodiment is characterized by the use of a disc-shaped sample container 60. This sample container 60 is made of a transparent material, such as plastic or glass, and is configured to be rotated by a drive motor (not shown). The sample which contains microparticles is applied to the top surface of the sample container 60.

Located below the sample container 60 is a multi-convergence illuminator 62, which casts a linear beam of light onto an area which radially extends from the center of the lower surface of the sample container 60. Located above the sample container 60 is a measurement device 64 for performing a measurement of the scattered light originating from the microparticles in the sample applied to the top surface of the sample container 60. For example, the measurement device 64 includes an objective lens, first and second transmission portions, a cylindrical lens and a detector as described in the first embodiment, to measure the spectral characteristic of the scattered light.

For example, the fourth embodiment is suitable as a device for detecting erythrocytes infected with plasmodium contained in a blood sample. Malaria is one of the infectious diseases which overseas travelers may develop. The disease is contracted by an injection of plasmodium into a human body by anopheles vectors. A method for its diagnosis is to detect erythrocytes infected with plasmodium. In an early phase of infection, it is difficult to detect the infected erythrocytes because their percentage in the entire amount of erythrocytes is extremely low, i.e. 1 to 2%. However, detection of the infected erythrocytes by an early-phase diagnosis is desired, since an increase in the percentage of the infected erythrocytes means an increase in the death rate.

In the present embodiment, the spectral characteristic of the erythrocytes contained in a blood sample can be efficiently measured by applying the sample to the top surface of the sample container 60 in the form of a film whose thickness is approximately equal to the size of one erythrocyte.

FIGS. 13A-13D show one example of the result of a measurement performed on a blood sample containing erythrocytes infected with plasmodium. These figures demonstrate that a specific absorption of light which cannot be observed with normal erythrocytes is observed with erythrocytes infected with plasmodium.

Fifth Embodiment

Figure 14A:
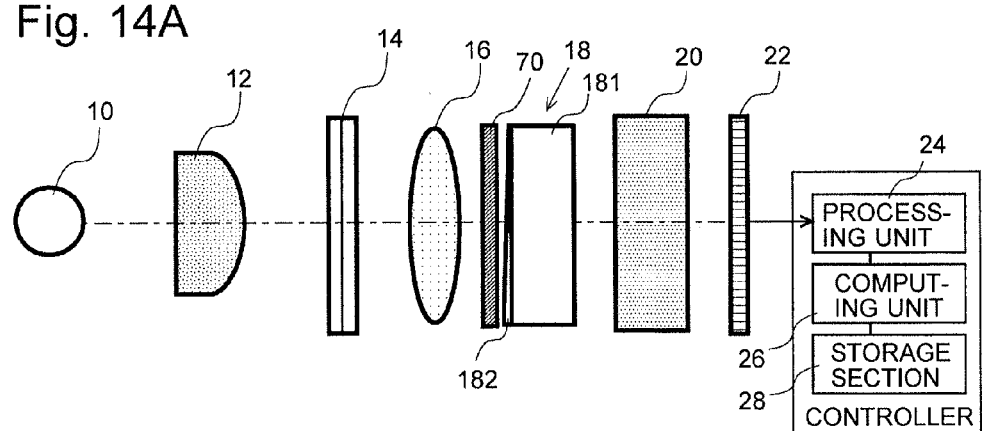
FIGS. 14A and 14B are model diagrams showing a microparticle measurement device according to the fifth embodiment of the present invention, where
Figure 14B:
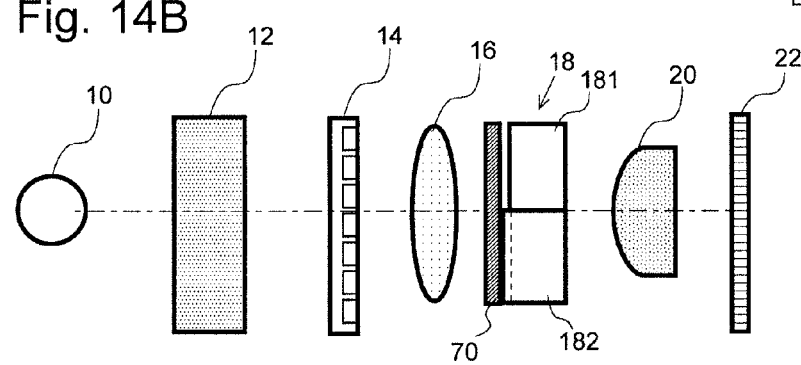

A microparticle measurement device according to the firth embodiment of the present invention is described with reference to FIGS. 14A and 14B. The present embodiment is a Raman spectroscopic analyzer for performing a quantitative and/or qualitative analysis of microparticles contained in a liquid sample by detecting Raman scattered light originating from those microparticles. In the present embodiment, a filter 70 is provided on the entrance side of the transmission phase shifter 18 in place of the shielding plate 30 (see FIG. 1). The other components are the same as those of the microparticle measurement device of the present embodiment.

The filter 70 is located on the optical path between the objective lens 16 and the phase shifter 18. The filter has such a size and shape that it entirely covers the entrance surface of the first transmission portion 181 and that of the second transmission portion 182 constituting the phase shifter 18. Accordingly, the light travelling from the detection windows 143 of the multi-flow channel 14 through the objective lens 16 toward the first and second transmission portions 181 and 182 initially falls onto the filter 70, and only the light which can pass through this filter 70 enters the first and second transmission portions 181 and 182.

The filter 70 is a notch filter that blocks the light incident from the light source onto the detection windows 143 of the multi-flow channel 14 (excitation light) and allows other wavelengths of light to pass through. Therefore, the excitation light which directly passes through the detection windows 143 of the multi-flow channel 14 among the light emitted from the light source, and the light which has the same wavelength as the excitation light among the light originating from the microparticles irradiated with the excitation light, are blocked by this filter, whereas the Raman scattered light, which has a different wavelength from the excitation light, is allowed to enter the phase shifter 18. As explained earlier, the light originating from microparticles becomes scattered light with a certain breadth and falls onto the entrance surfaces of both the first and second transmission portions 181 and 182. Accordingly, in the present embodiment, the spectral characteristic of the Raman scattered light can be obtained.

Raman scattered light is a kind of scattered light resulting from an interaction between a substance and light. In most cases, scattered light is Rayleigh scattered light; i.e. it has the same wavelength as the excitation light. However, a fraction of the scattered light emerges as Raman scattered light having a different wavelength from the excitation light. The amount of energy corresponding to the difference in wavelength between the Raman scattered light and the excitation light reflects the amount of energy of the natural vibration of the substance. Therefore, by determining the amount of this energy, it is possible to identify the substance. The quantity of the substance can also be determined from the intensity of the Raman scattered light. Accordingly, it is possible to perform a qualitative and/or quantitative analysis of microparticles contained in a liquid sample by irradiating the sample with excitation light, detecting the Raman scattered light originating from the irradiated microparticles, and obtaining its spectral characteristic.

As compared to the Rayleigh scattered light or excitation light, the Raman scattered light is extremely feeble. The use of the filter 70 which removes the excitation light and Rayleigh scattered light improves the detection sensitivity for the Raman scattered light.

In the microparticle measurement device according to the present embodiment, a laser light source which produces monochromatic light is preferable as the light source, such as a solid laser (e.g. YAG laser or YVO4 laser) or gas laser (e.g. Ar laser). As the detector, a two-dimensional array device composed of photoelectron multiplier tubes may also be used as well as the two-dimensional array device 22 consisting of a CCD camera described in the first embodiment.

As the filter 70 in the previously described embodiment, an edge filter may be used in place of the notch filter. For example, the excitation light can also be removed by the combination of an edge filter (long-pass filter) which allows the passage of light at wavelengths longer than the lower limit value of the wavelength band of the Raman scattered light and another edge filter (short-pass filter) which allows the passage of light at wavelengths shorter than the upper limit of the wavelength band of the Raman scattered light.

The microparticle measurement device according to the present embodiment can also be applied in a fluorescence spectrometer for performing a qualitative and quantitative analysis of microparticles in a sample based on the spectral characteristic of the fluorescence emitted from the microparticles due to irradiation with excitation light.

A fluorescent emission is a phenomenon in which an electron in a substance irradiated with a specific wavelength of excitation light absorbs energy from the excitation light and then releases the energy in the form of light when returning from the excited state to the ground state. The difference between the excitation wavelength and the fluorescence wavelength reflects the difference in the energy level between the excited state and the ground state. Therefore, it is possible to identify the substance by determining the fluorescence wavelength, and to determine the quantity of the substance from the fluorescence intensity. If the sample contains cells or microorganisms labelled with a fluorescent dye, or minerals which can emit fluorescence, or other similar microparticles, it is possible to perform a qualitative and/or quantitative analysis of the microparticles in the sample by irradiating the sample with excitation light, detecting the fluorescence emitted from the irradiated microparticles, and obtaining its spectral characteristic. Since the fluorescence wavelength is normally longer than the excitation wavelength, the detection sensitivity of the fluorescence can be improved by using, as the filter 70, an edge filter (long-pass filter) which blocks light at the wavelengths shorter than the excitation wavelength.

The present invention is not limited to the previously described embodiments but allows various modifications. For example, in place of the cylindrical lens 12 used for converting the light from the light source 10 into a linear beam of light in the first through fifth embodiments, a concave mirror may be used to convert the light from the light source 10 into a linear beam of light.

In the second and fifth embodiments, the optical member for converging the light from the light source onto the detection windows 143 (e.g. the cylindrical lens or concave mirror) is dispensable. For example, a member for shielding the multi-flow channel 14 from light within the areas other than the detection windows 143 may be provided to prevent the incidence of light from the light source 10 onto those areas. A light source which produces a linear beam of light whose shape corresponds to the detection windows 143 may also be used.

Figure 15A:
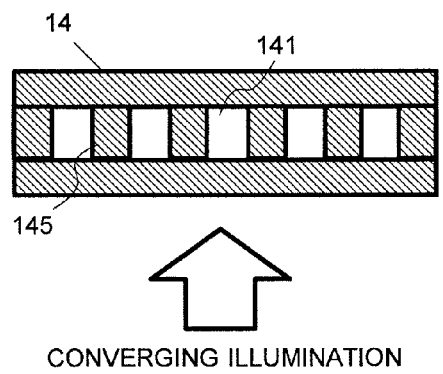
FIGS. 15A and 15B show variations of the multi-flow channel.
Figure 15B:
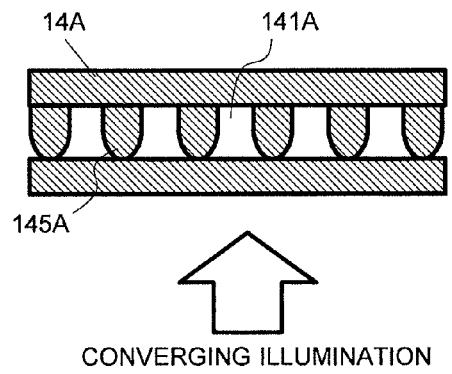

FIG. 15A is a vertical sectional side view of the multi-flow channel 14 used in the first through fifth embodiments, while FIG. 15B is a vertical sectional side view of a multi-flow channel 14A according to one variation. As shown in FIGS. 15A and 15B, the partition members 145 dividing the inner space of the multi-flow channel 14 have a flat end face on the light entrance side, whereas the partition members 145A in the multi-flow channel 14A have a curved end face on the entrance side. Due to such a structural difference, the multi-flow channel 14A, as compared to the multi-flow channel 14, allows a smaller amount of scattered light to occur due to the incident light striking the end face of the partition members 145A.

In the third embodiment using the reflection phase shifter 50, the filter 70 may be placed on the optical path between the reflection phase shifter 50 and the objective lens 16. In this case, the non-reflection areas 521 and 531 formed on the first and second reflection planes 52 and 53 can be omitted.

Although the device described in any of the previous embodiments is an independent microparticle measurement device, a flow cytometer or cell sorter can also be constructed by providing, on the downstream side of the microparticle measurement device, a means for sorting the microparticles contained in the sample by their spectral characteristics and a means for separately collecting the sorted microparticles.

REFERENCE SIGNS LIST

10 . . . Light Source
12 . . . Cylindrical Lens
14 . . . Multi-Flow Channel
  141, 141A . . . Flow Channel
  142 . . . Plate
  143 . . . Detection Window
16 . . . Objective Lens
18 . . . Transmission Phase Shifter
  181 . . . First Transmission Portion
  182 . . . Second Transmission Portion
20 . . . Cylindrical Lens (Imaging Lens)
22 . . . Two-Dimensional Photo-Detection Device
24 . . . Processing Unit
26 . . . Computing Unit
28 . . . Storage Section
51 . . . Beam Splitter
52 . . . First Reflection Plane
  521 . . . First Non-Reflection Area
53 . . . Second Reflection Plane
  531 . . . Second Non-Reflection Area
60 . . . Sample Container
70 . . . Filter
P . . . Microparticle

The invention claimed is:
1. A microparticle measurement device, comprising:
  a) a transparent sample container for holding a sample containing microparticles;
  b) a light-casting device for casting a light onto a linear area of the sample held in the sample container;
  c) a splitting optical system for splitting measurement light originating from a microparticle in the linear area into a first measurement beam and a second measurement beam;

d) an optical path difference creator for creating an optical path difference between the first measurement beam and the second measurement beam;
e) a cylindrical lens for converging the first measurement beam and the second measurement beam onto a same straight line to make the two beams interfere with each other;
f) a detector for detecting an intensity distribution of an interference light formed by the first measurement beam and the second measurement beam along a longitudinal direction of the same straight line; and
g) a processor for producing an interferogram of the light originating from the microparticle based on the intensity distribution of the interference light detected by the detector, and for obtaining a spectrum by Fourier-transforming the interferogram, and the microparticle measurement device further comprising,
a split prevention device for preventing light which is emitted from the light-casting device and passing through the sample container from being split by the splitting optical system.

2. The microparticle measurement device according to claim 1, wherein:
the splitting optical system comprises:
an optical member having a first transmission portion with an entrance surface and an exit surface parallel to each other, a second transmission portion, located next to the first transmission portion, having an entrance surface and an exit surface forming a wedge-like shape with one of the two surfaces inclined to the other, as well as a non-transmission portion which does not allow passage of light; and
an optical element for shaping the measurement light originating from the microparticle irradiated with the light from the light-casting device into a parallel beam falling onto both the entrance surface of the first transmission portion and the entrance surface of the second transmission portion, and for making the light which is emitted from the light-casting device and passing through the sample container fall onto the non-transmission portion;
the non-transmission portion constitutes the split prevention device; and
the first transmission portion and the second transmission portion constitute the optical path difference creator.

3. The microparticle measurement device according to claim 1, wherein:
the splitting optical system comprises:
an optical member having a first transmission portion with an entrance surface and an exit surface parallel to each other, as well as a second transmission portion, located next to the first transmission portion, having an entrance surface and an exit surface forming a wedge-like shape with one of the two surfaces inclined to the other; and
an optical element for shaping the measurement light originating from the microparticle irradiated with the light from the light-casting device into a parallel beam falling onto both the entrance surface of the first transmission portion and the entrance surface of the second transmission portion;
the split prevention device comprises a filter, located between the optical element and the entrance surfaces of the first and second transmission portions, for blocking the light from the light-casting device; and
the first transmission portion and the second transmission portion constitute the optical path difference creator.

4. The microparticle measurement device according to claim 1, wherein:
the splitting optical system comprises: a reflection optical member having a first reflection plane with a first non-reflection area and a second reflection plane with a second non-reflection area; and an optical element for shaping the measurement light originating from the microparticle irradiated with the light from the light-casting device into a parallel beam, for splitting the parallel beam into two beams respectively falling onto the first reflection plane and the second reflection plane, and for making the light which is emitted from the light-casting device and passing through the sample container fall onto the first non-reflection area and the second non-reflection area;
the first non-reflection area and the second non-reflection area constitute the split prevention device; and
the optical path difference creator comprises a driving device for moving the first reflection plane and the second reflection plane relative to each other.

5. The microparticle measurement device according to claim 1, wherein:
the splitting optical system comprises: a reflection optical member having a first reflection plane with a first non-reflection area and a second reflection plane with a second non-reflection area; and an optical element for shaping the measurement light originating from the microparticle irradiated with the light from the light-casting device into a parallel beam, for splitting the parallel beam into two beams respectively falling onto the first reflection plane and the second reflection plane, and for making the light which is emitted from the light-casting device and passing through the sample container fall onto the first non-reflection area and the second non-reflection area;
the first non-reflection area and the second non-reflection area constitute the split prevention device; and
the optical path difference creator is realized by making one of the first and second reflection planes inclined from a plane perpendicular to an optical axis of the measurement beams.

6. The microparticle measurement device according to claim 1, wherein:
the sample container is provided with a measurement channel with a plurality of flow channels arranged parallel to each other, with a size of the flow channels determined so as to allow the microparticles to flow in parallel, with one microparticle in each channel; and
the light-casting device casts the linear beam of light onto a linear area encompassing the plurality of flow channels.

7. The microparticle measurement device according to claim 1, wherein:
the sample container is a holder plate in a form of a disc having a top surface to which a sample containing microparticles is to be applied;
a rotating device for rotating the holder plate about a center of the disc is additionally provided; and
the light-casting device casts the linear beam of light which illuminates a linear area extending radially from the rotation center toward a circumferential edge of the holder plate.

8. The microparticle measurement device according to claim 2, wherein:
the sample container is provided with a measurement channel with a plurality of flow channels arranged parallel to each other, with a size of the flow channels determined so as to allow the microparticles to flow in parallel, with one microparticle in each channel; and the light-casting device casts the linear beam of light onto a linear area encompassing the plurality of flow channels.

9. The microparticle measurement device according to claim 3, wherein:

the sample container is provided with a measurement channel with a plurality of flow channels arranged parallel to each other, with a size of the flow channels determined so as to allow the microparticles to flow in parallel, with one microparticle in each channel; and the light-casting device casts the linear beam of light onto a linear area encompassing the plurality of flow channels.

10. The microparticle measurement device according to claim 4, wherein:

the sample container is provided with a measurement channel with a plurality of flow channels arranged parallel to each other, with a size of the flow channels determined so as to allow the microparticles to flow in parallel, with one microparticle in each channel; and the light-casting device casts the linear beam of light onto a linear area encompassing the plurality of flow channels.

11. The microparticle measurement device according to claim 5, wherein:

the sample container is provided with a measurement channel with a plurality of flow channels arranged parallel to each other, with a size of the flow channels determined so as to allow the microparticles to flow in parallel, with one microparticle in each channel; and the light-casting device casts the linear beam of light onto a linear area encompassing the plurality of flow channels.

12. The microparticle measurement device according to claim 2, wherein:

the sample container is a holder plate in a form of a disc having a top surface to which a sample containing microparticles is to be applied;

a rotating device for rotating the holder plate about a center of the disc is additionally provided; and the light-casting device casts the linear beam of light which illuminates a linear area extending radially from the rotation center toward a circumferential edge of the holder plate.

13. The microparticle measurement device according to claim 3, wherein:

the sample container is a holder plate in a form of a disc having a top surface to which a sample containing microparticles is to be applied;

a rotating device for rotating the holder plate about a center of the disc is additionally provided; and the light-casting device casts the linear beam of light which illuminates a linear area extending radially from the rotation center toward a circumferential edge of the holder plate.

14. The microparticle measurement device according to claim 4, wherein:

the sample container is a holder plate in a form of a disc having a top surface to which a sample containing microparticles is to be applied;

a rotating device for rotating the holder plate about a center of the disc is additionally provided; and the light-casting device casts the linear beam of light which illuminates a linear area extending radially from the rotation center toward a circumferential edge of the holder plate.

15. The microparticle measurement device according to claim 5, wherein:

the sample container is a holder plate in a form of a disc having a top surface to which a sample containing microparticles is to be applied;

a rotating device for rotating the holder plate about a center of the disc is additionally provided; and the light-casting device casts the linear beam of light which illuminates a linear area extending radially from the rotation center toward a circumferential edge of the holder plate.

* * * * *